United States Patent
Campbell et al.

(10) Patent No.: US 6,874,364 B1
(45) Date of Patent: Apr. 5, 2005

(54) SYSTEM FOR MONITORING MECHANICAL WAVES FROM A MOVING MACHINE

(75) Inventors: Jonathan Joseph Campbell, Brisbane (AU); Yi Liu, Sydney (AU); Victor Sharp, Sydney (AU); Steven John Spencer, Sydney (AU); Keith Russell Weller, Brisbane (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 0 days.

(21) Appl. No.: 10/019,307

(22) PCT Filed: Jul. 7, 2000

(86) PCT No.: PCT/AU00/00821

§ 371 (c)(1),
(2), (4) Date: Apr. 11, 2002

(87) PCT Pub. No.: WO01/03840

PCT Pub. Date: Jan. 18, 2001

(30) Foreign Application Priority Data

Jul. 9, 1999 (AU) .............................................. PQ1524

(51) Int. Cl.[7] .............................................. G01N 29/00
(52) U.S. Cl. .............................. 73/593; 73/649; 73/659; 73/660
(58) Field of Search .......................... 73/593, 597, 592, 73/649, 660, 661, 662, 658, 587, 659

(56) References Cited

U.S. PATENT DOCUMENTS 3,690,570 A    9/1972  Root ............................ 241/34
4,237,454 A *  12/1980 Meyer ......................... 340/682
6,161,962 A *  12/2000 French et al. ................ 384/459
6,189,384 B1 * 2/2001  Piety et al. .................... 73/592
6,297,742 B1 * 10/2001 Canada et al. .............. 340/635
6,484,109 B1 * 11/2002 Lofall .......................... 702/56
6,593,854 B2 * 7/2003  Brown ......................... 340/682

FOREIGN PATENT DOCUMENTS

DE          4215455 A1    11/1993

OTHER PUBLICATIONS

Derwent Abstract Accession No. K. 1137E/30, SU869809A. (Kaza Poly), Oct. 7, 1981.
Derwent Abstract Accession No. 85–235616/38, SU1146084A, (Kriv Ore Mining), Mar. 23, 1985.
Derwent Abstract Accession No. D5692C/16, SU67923A (As Kaza Metal Enric), Aug. 15, 1979.

* cited by examiner

Primary Examiner—Hezron Williams
Assistant Examiner—Jacques M. Saint-Surin
(74) Attorney, Agent, or Firm—Jacobson Holman

(57) ABSTRACT

A system for monitoring mechanical waves from a machine which in operation has moving particulate matter therein, the system including at least one sensor located on the machine at a location away from the central axis of the machine, the sensors being for sensing acoustic waves and including a transmitter for transmitting signals representing the sensed mechanical waves to a receiver at a location remote from the sensor(s), a data processor connected to the receiver for receiving signals from the receiver which signals represent the mechanical waves and processing the signals to produce output signals for display on a display means, wherein the output signals for display represent one or more parameters indicative of mechanical waves emitted from the machine over a predetermined period of time.

19 Claims, 17 Drawing Sheets

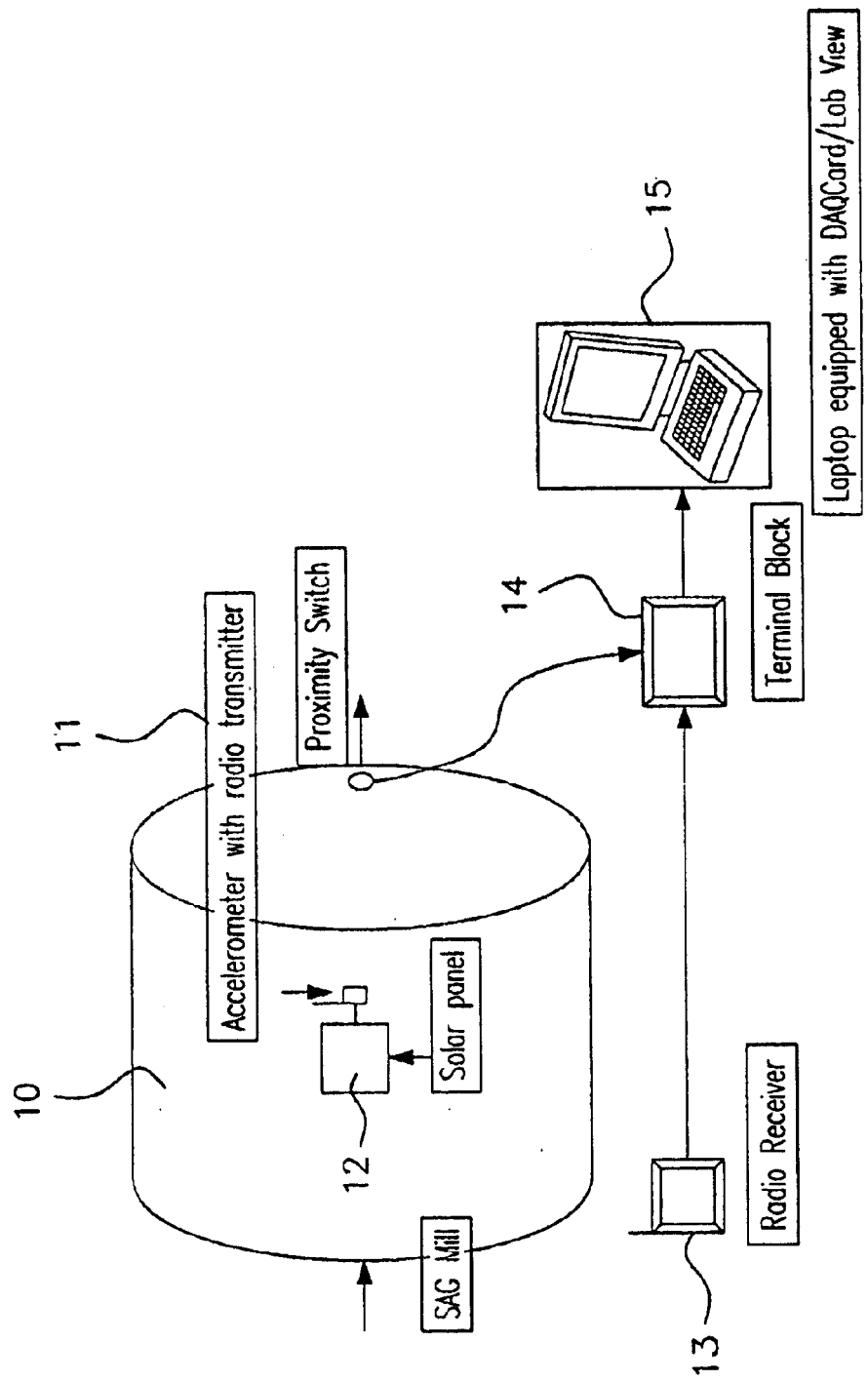

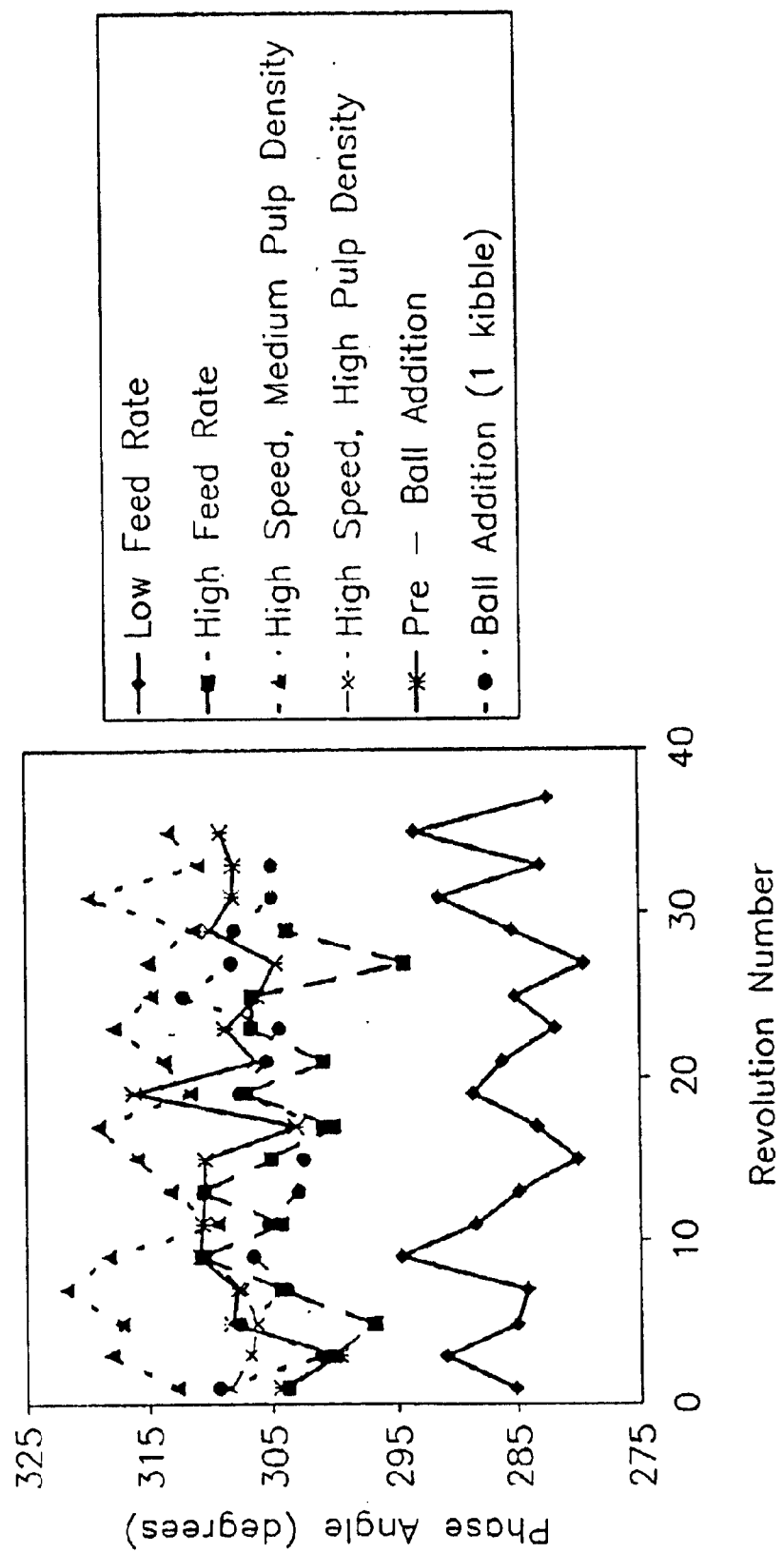

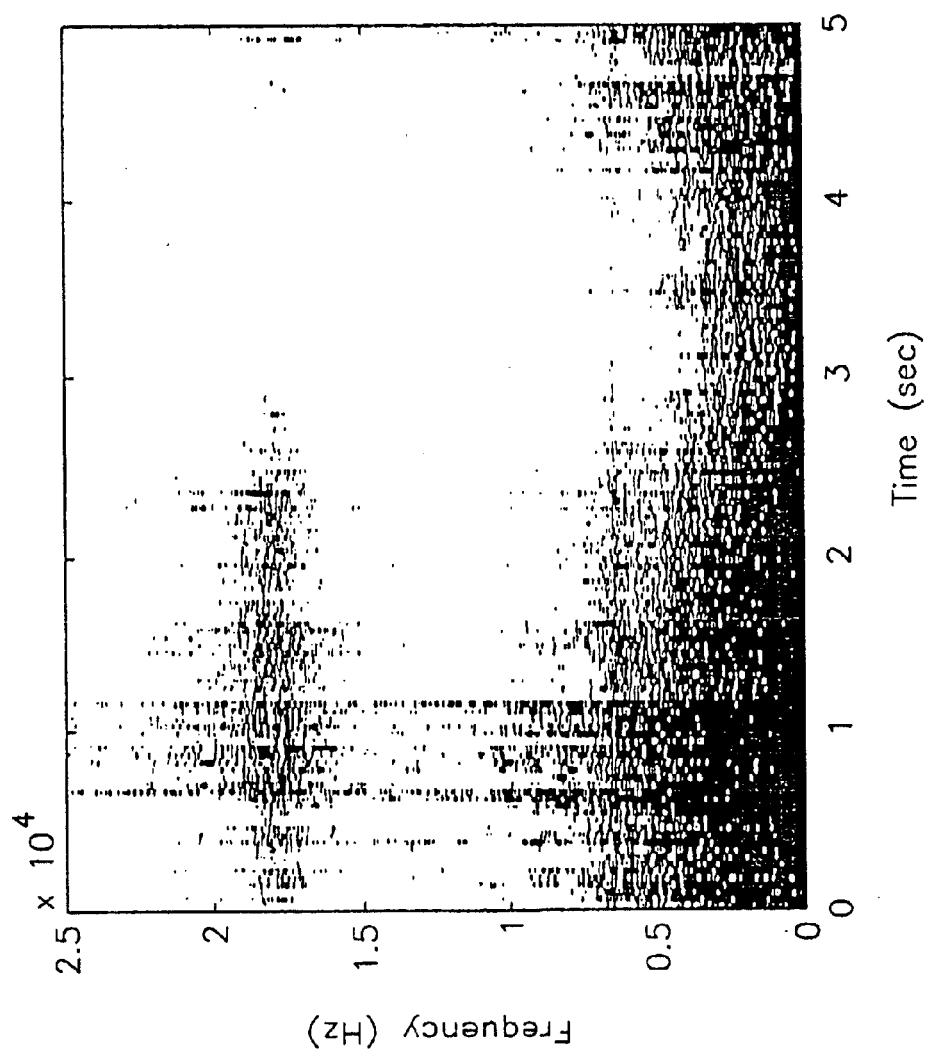

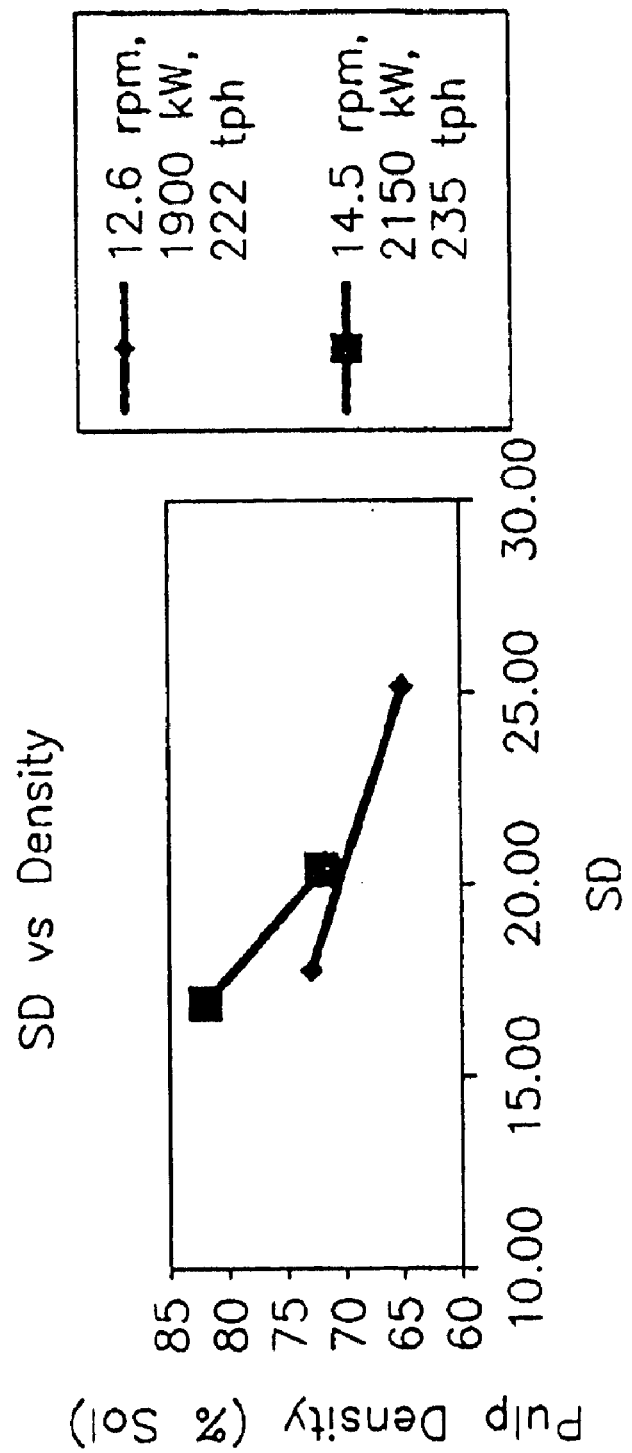

SYSTEM FOR MONITORING MECHANICAL WAVES FROM A MOVING MACHINE

This is a nationalization of PCT/AU00/00821 filed Jul. 7, 2000 and published in English.

FIELD OF THE INVENTION

This invention relates to the monitoring and analysis of surface vibration waves generated by the operation of material processing equipment. 'The invention is of particular application to the non-intrusive monitoring and control of mineral processing equipment, such as tumbling mills, where the equipment component being monitored is in motion. The invention also has application to equipment with stationary components but moving mineral particles or pulp flows, such as crushers and hydrocyclones. The invention was initially developed for condition monitoring and process control of Semi-Autogenous Grinding (SAG) mills.

BACKGROUND OF THE INVENTION

Acoustic emissions and surface vibrations monitoring, have previously been used to investigate and control the performance of mineral processing unit operations. Control of power draft in autogenous grinding (AG) mills and SAG mills has traditionally been via load cells estimating the charge mass. However, acoustic emissions from dual microphone systems have been used to monitor the changing level of impact of the charge on an AG mill shell. A pair of microphones were mounted at approximately 30° from the bottom and 30° from the centre line of the mill. The position of the microphones was such that the upper unit was above the normal level of charge impact on the liner while the lower unit was below the same. If the load level rises in the mill, the point of impact moves toward the upper microphone and away from the lower. If the load level drops, the converse applies. Therefore changes in load level are registered by variation in the comparative sound intensity at the two microphones. The resulting estimate of the load volume is correlated with the power draft and used to control the feed rate in order to maintain optimal milling conditions and maximum power draft. It was shown that microphone signals are much more sensitive to load change than the load cell. However, the method is crude in that it uses sound intensity at only two fixed points outside the mill. The intensity of sound at these two positions may be considerably influenced by events both outside the mill and at a variety of locations within the mill. The technique therefore only permits qualitative investigation of the state of the charge inside the mill.

Acoustic emissions are also known to be indicators of pulp density and viscosity. The dual microphone study of AG mill acoustic emissions showed that the sound intensity emanating from the charge region (lower microphone) was correlated with the pulp density. The lower microphone sound intensity was used to control water addition rate. Low pulp density was thought to result in higher transmission of noise and increased media/media and media/liner collision events. Meanwhile at higher pulp density grinding action was thought to be inhibited by the increased pulp viscosity, reflected in lower noise intensity. Estimation of effective pulp density and viscosity via the magnitude of acoustic emissions has also been achieved for laboratory batch ball mills. Results suggest that changes in mill noise can be used to identify the pulp rheological regime and potentially used to optimise grinding efficiency. Mill sound noise has also been shown to indicate charge size distribution, ore breakage rates, and ore character in batch ball mills (Watson, 1985; Watson and Morrison, 1985).

Acoustic emissions monitoring has also been used to analyse hydrocyclone performance. A shear structure piezoelectric type acoustic sensor was mounted halfway along the conical section of a 5" hydrocyclone body. The digitised signal was sampled at 2000 Hz and a Past Fourier Transform (FFT) algorithm used to derive the Power Spectral Density function (PSD) for analysis of acoustic emission characteristics in the frequency domain. Features of acoustic emissions were analysed for varying feed solids concentrations and pressure. Results indicated significant spectral features in the frequency range from DC to about 50 Hz and between 30 and 45 Hz. The height of these spectral features was sensitive to operating conditions. It was conjectured that the spectral structure is related to features of the hydrodynamics inside the hydrocyclone local to the sensor. A stepwise regression analysis technique was used to derive linear relationships between the operating parameters of the cyclone and the spectral and statistical characteristics of the acoustic emissions. The signal measures used in this analysis were for the time domain maxima, mean, standard deviation, rootmean-square, skewness and kurtosis, and for the frequency domain the first 52 spectral components of the PSI). The model was then used for reasonable predictions of hydrocyclone feed pressure, solids concentration, mass and volume flow rates and underflow concentration. This investigation showed that non-invasive acoustic emission measurement coupled with multivariate statistical analysis techniques are a useful tool for monitoring the bulk characteristics of both process and equipment, in this case hydrocyclone operation.

Vibration monitoring and signal analysis have been used to study the feed distribution characteristics of parallel Dense Medium (DM) cyclones in a coal preparation plant. The method is based on the concept that the monitoring of vibrations on the external surface of the cyclone can yield the frequency and strength of particle impacts (particularly for larger particles near entry and exit points). Accelerometers for measuring vibrational accelerations were mounted near the feed inlet, underflow spigot and overflow cap. Relatively large vibrations were noted in the region of the overflow cap, reflecting the energy of particle/wall impacts in that region due to the flow regime within the cyclone. Results indicated that vibration measurements are a superposition of a large number of transients caused by individual particle impacts.

SUMMARY OF THE INVENTION

According to the present invention a system is provided which is capable of monitoring acoustic emissions from a moving machine.

The invention includes within its scope systems for monitoring moving substances within a stationery or moving machine.

The system in broad terms is directed at monitoring mechanical wave emissions from inside the machine and the surface of the machine, as well as associated components of the machine which are affected by the machine's operation.

According to a first aspect, the invention provides a system for monitoring mechanical waves from a machine which in operation has moving particulate matter therein, the system including at least one sensor located on the machine at a location away from the central axis of the machine, the sensor (s) being for sensing mechanical waves and including a transmitter for transmitting signals representing the sensed mechanical waves to a receiver at a location remote from the sensor(s), a data processor connected to the receiver for receiving signals from the receiver which signals represent the mechanical waves and processing the signals to produce output signals for display on a display means, wherein the output signals for display represent one or more parameters indicative of mechanical waves emitted from the machine over a predetermined period of time.

It is preferred that the output signals represent a number of acoustic events occurring within the machine, amplitudes of the acoustic events and data relating to the position of the acoustic events.

It is preferred that the system includes a plurality of sensors each for detecting acoustic emissions from inside the machine and from the surface of the machine.

It is preferred that the system includes a plurality of sensors spaced around the periphery of the machine to enable polar co-ordinates of the origin of emissions to be located.

It is preferred that the sensors are equispaced around the periphery of the machine.

According to one embodiment of the invention sensors are arranged in an array around the machine and along the length of the machine to enable a three-dimensional co-ordinate axis to be plotted of the location of the origin of emissions from the machine.

It is preferred that these sensors are removably attached to the outer surface of the machine.

According to one embodiment the transmitter associated with each sensor is located away from a detector part of the sensor.

According to one embodiment one or more transmitters of the sensors are removably attachable to the machine.

It is preferred that the system includes at least one proximity detector for monitoring the location of the sensors at a predetermined time.

According to one variation of the present invention the data processor includes a timing means for calculating the location of the sensor(s) at a predetermined time.

It is preferred that the timing means output data relating to the position of the sensor(s) at a particular time, based on data received either from the proximity detector(s) or/and data received relating to the movement of the machine.

It is preferred that the data processor receives signals from the receiver, which signals include data relating to the frequency of vibrational events occurring within the machine and the amplitude of the vibrational events at particular locations within the machine.

It is preferred that the sensor(s) includes an accelerometer.

It is preferred that the sensor includes a power supply.

The power supply may be a solar cell.

According to another embodiment of the present invention the power supply is a 12 volt gel cell rechargeable battery.

Battery charging may be achieved using two solar panels mounted on opposite sides of the mill or alternatively other recharging methods include an inertial generator, offtake from the electric drive, or some other source that provides a continuous power supply.

According to another aspect of the present invention there is provided a method of analysing operational parameters of a machine having a moving particulate material therein, the method including the steps of recording data representing a number of mechanical events occurring within the machine over a predetermined period of time, the amplitude of the mechanical events occurring over the predetermined period of time and positional data relating to the position of the mechanical events occurring within the machine, displaying a graphical representation of the recorded data, the graphical representation including parameters relating to the number of mechanical events, the amplitude of mechanical events and the position of mechanical events occurring within the machine during the machines operation.

Preferably the mechanical events include mechanical events.

It is preferred that the graphical representation includes data on the radial and angular position of each vibrational event.

Preferably the graphical representation shows the number of vibrational events on a polar co-ordinate graph.

According to one embodiment the step of displaying includes displaying a histogram of variables relating to the number of vibrational events occurring over the predetermined time.

The present invention also includes within its scope graphical representation of the recorded data in a rectilinear co-ordinate system and three dimensional co-ordinate system.

According to one embodiment of the present invention the step of displaying includes displaying a graphical representation of the recorded data on a data processing monitor using 3D graphics which simulate the machine and provide a graphical representation of the moving particulate material within the machine.

It is preferred that the step of displaying includes highlighting regions within the machine which have vibrational events liable to cause maximum damage to a component of the machine.

According to another variation of the present invention the graphical representation includes a colour scheme for colouring regions of the graphical representation according to features of vibrational events occurring at positions of the vibrational events.

According to another aspect of the present invention there is provided a method of controlling operational parameters of a machine having a moveable substance therein, the method including the steps of recording data representing a number of mechanical events occurring within a machine over a predetermined period of time, amplitude and/or frequency of the mechanical events occurring over the predetermined period of time and position data relating to the position of the mechanical events over the predetermined period of time, determining zones within the machine which are subject to predetermined levels of wear and altering the machine operational characteristics to reduce the levels of wear for the zones.

Preferably the mechanical events includes vibrational events.

It is preferred that the step of determining zones, includes processing the recorded data with data relating to the substance or substances within the machine, and dynamic properties of the substances) to produce a level of wear indication parameter for a plurality of zones within the machine.

It is preferred that the method includes operating a data processor which includes recorded model data relating to wear characteristics of the machine as a function of a plurality of parameters which may include one or more combinations of the following:

The number of vibrational events occurring within the machine, the amplitude of the vibrational events occurring within the machine, the position of the vibrational events occurring within the machine, the mass of the particulate material and other material substance(s) within the machine, the size of the particulate matter the machine, the volume of particulate matter within the machine, the volume of space within the machine, the shape of the machine and other parameters which are likely to affect the wear characteristics of the machine.

Alternatively the method of controlling the machine includes determining the efficiency of operation of the operational characteristics of the machine.

It is preferred that the method includes the step of processing the recorded data with other data relating to characteristics of the particulate matter and machine to determine the efficiency of operating characteristics of the machine.

The operating characteristics could include the efficiency of a crushing operation over a predetermined period of time.

It is preferred that the method includes the step of increasing or decreasing the speed of operation of the machine, including rotation or reciprocating motion of the machine and/or alteration of rate of feed of particulate matter to the inside of the machine.

It is preferred that the method includes the step of maximising a predetermined operational parameter of the machine. This may include maximising the amount of crushing of a material within a machine that is a crusher. Preferably the graphical representation includes any one or more of the following, Fourier analysis, histogram, signal moment, surface vibration event analysis and wavelet analysis. Other analysis techniques include Sepstrum and Homomorphic Deconvolution techniques of non-linear signal processing.

Preferably the method includes the step of truncating data recorded to an integral number of mill rotation periods.

The method preferably includes the step of recording data representing frequency of vibrational events occurring over a predetermined period of time.

The method may also include the step of measuring or monitoring volumetric load in the machine by identifying the toe and shoulder positions of particular matter within the machine.

Preferably the method includes obtaining a polar co-ordinate plot of the volumetric of particulate matter within the machine.

It is preferred that the recorded data is processed to provide a display of the location of high energy events throughout a polar plot of the machine.

It is preferred that the method includes recording data for different operational parameters of the machine including speed of revolution.

Preferably the method includes identifying a range of angles within which greater numbers/amplitude/frequency of vibrational or other mechanical events are occurring.

It is preferred that a value $$f = \frac{(\theta - \sin\theta)}{2\pi}$$

is able to be produced by the method to provide a first approximation for volumetric filling of the machine, where θ is the angle (radiance) between the toe and shoulder positions of the particulate material.

It is preferred that the method includes producing a preferred operational speed for the machine in order to minimise the number/amplitude/frequency of vibrational events occurring within the machine for a particular value of θ.

Preferably the method of controlling operational parameters of a machine includes using a value of F for a particular amount of particulate matter within a machine in order to identify a preferred speed of operation of the machine whereby the number/amplitude/frequency of vibrational events occurring within the machine is minimised.

Minimsation of number/amplitude/frequency of vibrational events occurring within the machine can be produced by choosing an operational speed of the machine which minimises the value of f.

It is preferred that impact on the machine caused by the toe and shoulder of the particulate matter is able to be monitored in order to minimise wear and tear on the liner or other parts of the machine.

BRIEF DESCRIPTION OF THE DRAWINGS

Preferred embodiments of the present invention will now be described by way of example with reference to the accompanying drawings in which:

FIG. 2 shows a schematic of a basic system for monitoring acoustic emissions from a rotating machine;

FIG. 4c shows a diagram of amplitude weighted average event phase angle as a function of revolution number and operating conditions;

FIG. 7d shows a spectrogram plot upto 25,000 Hz ($2^{12}$ FFT length and Hanning windowing, $2^{11}$ number of samples overlap and nil detrending);

FIG. 9 shows a graphical representation of pulp density (percent solids) as a function of the standard deviation of surface vibrations for two different sets of mill conditions.

PREFERRED EMBODIMENT OF THE INVENTION

Figure 1:
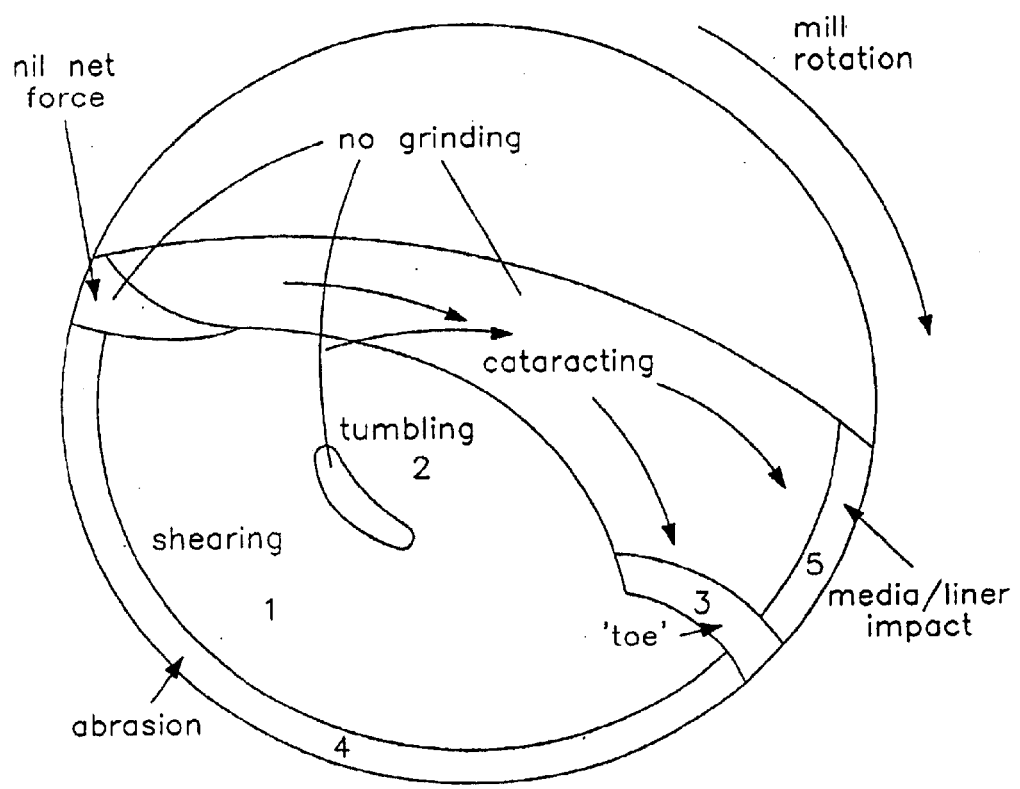
FIG. 1 shows a schematic of grinding media behaviour in a SAG Mill rotating at abnormally high speed.

An example of a system for monitoring vibrational events occurring within an SAG 10 Mill will now be described.

An SAG Mill 10 consists of a metal cylindrical drum containing metallic ball bearings and particulate matter to be crushed.

The surface of the mill 10 is provided with an accelerometer 11 which is movably fixed thereto and includes a radio transmitter.

A solar panel 12 is electrically connected to the accelerometer 11 to provide a power supply.

A radio receiver 13 is connected to a stationery part of the SAG Mill framework and receives data transmitted by the radio transmitter of the accelerometer 11.

The radio receiver is hardwired to a terminal block 14 and a laptop computer 15 is able to be connected to the terminal block to receive data sensed by the accelerometer.

One or more proximity switches are located on the rotating part of the mill 10 to enable the position of the accelerometer to be located relative to the rate of rotation of the mill.

The operation of a SAG mill 10 results in the generation of high frequency surface waves on the outside of the rotating shell due to collision events within the mill. Monitoring of surface waves with a sensitive accelerometer therefore provides information on events inside the mill, particularly impacts of grinding media on the liner The grinding media is defined here as non-ore (often steel balls) and ore particles (the larger size fractions of which contribute to impact grinding). However, measurements of surface vibrations on the outside of the shell do not simply reflect local impact events on the inside of the liner. All of the components of the mill behave to some extent as elastic media, permitting the propagation of waves generated by collision events within the mill, 'flexing' of the mill shell during rotation and external sources such as the drive motor and girth gear. Transverse surface vibrational waves propagate around the inside of the liner and around the outside of the shell. Meanwhile longitudinal sound waves travel through the charge and between the liner and shell. An accelerometer mounted on. the outside of the shell registers normal acceleration due to waves transversely propagating around the shell. These waves are damped in accordance with the properties of the elastic media between the point of wave registration and the origin of the causative event. Hence vibrational events as measured by an accelerometer can be expected to be due to causative events over a limited range of locations within the mill and associated assembly. However, for preliminary analysis it is assumed that the vibrations are locally, generated by collision events inside the mill, adjacent to the accelerometer.

The behaviour of grinding media in a rotating SAG mill 10 is usually characterised in a similar manner to balls in a ball mill. Grinding regions are expected to consist of the following (see FIG. 1):

shearing layers of media near the base of the charge article shatter and cleavage (region 1).

tumbling media from high to low gravitational potential near the top of the charge causing particle shatter (region 2).

cataracting media impacting in the 'toe' region of the charge causing particle shatter (region 3).

some abrasion breakage between the grinding media and the liner in the contact region between the charge and the liner between the "toe and shoulder" (nil net force) of the charge (region 4).

Higher mill rotational speeds cause cataracting grinding media to directly impact on the liner above the 'toe' of the charge (FIG. 1, section 5). Liner 'Wear is approximately proportional to the square of the mill speed and increases with grinding media size due to the consequent increase in impact energy. It is known that the presence of mineral slurry is very effective in damping the impact force of grinding media on the liner. Hence liner cracking is interpreted as evidence of a problem of excessive direct impact of grinding media on the liner. The lifter profile also plays a strong role in determining the trajectory of cataracting grinding media and hence both the location and energy of impact of the grinding media on the charge or the liner wall. A rectangular lifter profile is thought to result in the widest profile of cataracting events for a given mill speed and charge volume This could be interpreted as meaning that a rectangular lifter profile leads to the highest inherent likelihood of large impact events directly on the liner. The composition of the liner itself directly influences both impact and abrasion resistance. Use of a liner material that is strongly resistant to abrasion often results in low impact resistance and hence an increased propensity to cracking. Other causes of liner wear are corrosion (in wet mills) and abrasion. However, these sorts of wear are not expected to be manifested as liner cracking. A non-intrusive means of quantifying the spatial position and intensity of the various types of grinding behaviour in SAG mills would be very useful for process monitoring and control. SAG mill operators are very keen to use a technique that provides a reliable measure of mill load Monitoring of the frequency and spatial position of large energy particle impacts would also be very useful for monitoring and controlling SAG mill liner wear.

APPARATUS

The surface vibration monitoring system can be configured in two ways—basic or advanced. The following provides a description of each configuration.

Basic System

The surface vibration monitoring apparatus consists of a Bruel and Kjaer accelerometer type 4393 connected to a Bruel and Kjaer charge amplifier type 2634. The output from the charge amplifier is connected to a microphone beltpack transmitter (AKG type BT5 1) powered by a 12 volt gel-cell rechargeable battery. Battery recharging is achieved using two solar panels mounted on opposite sides of the mill. Transmitted data is received using a microphone wireless receiver (AKG type SR5 1) with two modified extended antennae.

Receiver output is connected to a terminal block and ribbon cable. The ribbon cable is connected to fast data acquisition PCMCIA DAQCard-Al-1 16E -4 linked to a laptop computer.

A magnetic proximity pad was mounted on the mill; at 3 o'clock looking from the discharge end. The detector/switch was mounted off the mill and connected to the terminal block mentioned above. The switching signal from the proximity detector is used as a trigger for logging of the accelerometer signal.

The software (written in LabView) can be triggered manually or digitally. Triggering occurs when the magnetic pad and detector/switch comes in close proximity as the mill rotates and a 5 volt signal changes to 0 volts. Data acquisition then begins with the data being read into a rolling buffer and stored into five data arrays. Acquisition rate is adjustable up to 100 k samples/s. At the end of the acquisition process, the mean of the arrays is calculated as well as the standard deviation. This; data is stored in a file retrieved using Excel and contains the following information:

Time in seconds from when the system first began logging.

Signal mean in volts.

Signal standard deviation in volts

Sample size.

Unprocessed raw data was also saved in binary format for further data processing analysis as mentioned later.

Advanced System

The advanced system includes the basic system described above plus one or more additional accelerometers and associated equipment. The accelerometers are of the same type as described above. The main difference with the advanced system is an improved radio transmission and reception apparatus to enable data acquisition down to lower frequency ranges (around 1 Hz). The apparatus consists of an Adam module digital radio modem and reception system linked to an on-mill computer that performs preliminary signal processing before transmission to the logging computer. The improved system can run in parallel beside the basic system and data is logged and saved on the same laptop. The advanced system requires extra power for operation so extra solar panels are required compared with the basic system. The advanced system can consist of multi-accelerometers either in basic or advanced configuration to investigate low frequency events, event spatial localisation, and events occurring on the ends of the mill. Signal data processing techniques are then used to determine surface vibration features for given operating conditions. A schematic of the basic system attached to the shell of a SAG mill is shown in FIG. 2.

EXPERIMENTAL DESIGN

Two series of surface vibrations monitoring runs were conducted on the SAG mill at the Red Dome gold mine, using the basic system of apparatus. The first was a limited series of test runs at different mill operating conditions essentially to test the system and establish that under severe plant duty the system produced data that could be processed. Qualitative evaluation of the data clearly indicate that features of the data (in the form of a voltage-time trace) changed at different operating conditions. Features identified were: the minimum signal strength, length of time between start of signal and proximity signal, length of time for events to return to background, maximum signal size, number and position of high frequency/high energy spikes, amplitude of high energy spikes and variation between successive revolutions. These results highlighted the necessity for further surface vibrations monitoring of the Red Dome SAG mill using a conditional experimental design so that the influence of only one variable could be measured in the context of changes in surface vibration features. Thus, this approach would better characterise the potential relationships between features and operating settings.

The second series of test runs at Red Dome conformed to the conditional experimental design approach. A total of 23 test runs were conducted to investigate how surface vibration features changed with one manipulated operating variable at a time. The manipulated operating variables were tonnage rate, mill speed, mill discharge density and ball addition. In addition to acquiring surface vibration information, both control system data and physical plant measurements were taken at each set of conditions to confirm test run validity.

Faster acquisition speeds were possible for the second series of tests and a range of data was collected at each manipulated mill condition. A 'normal' run was conducted first at a scan rate of $5\times10^4$ scans/s with raw data and statistical averages of the mean and standard deviation being saved. Then a 'fast' run, with acquisition rate increased to $1\times10^5$ scans/s, was conducted for a duration of $1\times10^6$ scans. Following the fast run, a run using the original LabView VI written for the first series of lest runs was conducted at the same speed as a 'normal' run listed above and saved to a binary file. Lastly, a 'long' run was conducted with the acquisition speed set at $5\times10^4$ scans/s for a duration of $1\times10^6$ scans. Listed below are the range of conditions for the manipulated operating variables:

Manipulated variable—tonnage (range 170–200 tph)
    Mill speed—11.8 rpm
    No ball addition
    Pulp density—72% solids w/w.

Manipulated variable—speed (range 12.3–13.8 rpm)
    Tonnage—2 10 tph
    No ball addition
    Pulp density—72% solids w/w.

Manipulated variable—ball addition (no-yes 1 kibble)
    Tonnage—2 10 tph
    Mill speed—13.8 rpm
    Pulp density—72% solids w/w.

Manipulated variable—pulp density (65–72% solids w/w)
    Tonnage—210 tph
    Mill speed—12.5 rpm
    No ball addition Manipulated variable—pulp density (72–82% solids wiw)
    Tonnage—210 tph
    Mill speed—14.5 rpm
    No ball addition A number of other tests were conducted at intermediate conditions for tonnage and speed within the range listed above.

Data Analysis Techniques

The goal of the data analysis techniques is to derive quantitative measures and qualitative visualisations based on the response of the accelerometer to shell vibrations that can be correlated with SAG mill operating conditions. This enables vibration measurements to be used for process condition monitoring and as an input to unit control. The measures are also useful for inference of the rate of liner wear as a function of operating conditions in with the SAG mill.

Surface vibrational waves as registered by an accelerometer are characterised by a wide variety of measures. The first step in data processing prior to deriving any of these measures is to truncate the data to an integral number of mill rotation periods. This is done in order to ensure that there is no bias in the data due to the sensor detecting changes in mill conditions as a function of rotational position of the outer shell.

The concept of a shell surface vibration event is important in the data processing. Such an event is defined as a positive deviation from nil accelerometer response. The amplitude is taken as the peak accelerometer response associated with a positive acceleration. This is in accordance with a propagating surface wave inducing a positive acceleration in an accelerometer corresponding to a normal stress outwards from the shell. It is hypothesised that collision events within the mill, particularly grinding media/liner events, will induce a strain that will propagate as a wave to the outside of the shell and be initially sensed as a positive acceleration. A wave train due to a collisional event should be composed of an initial relatively large, positive acceleration followed by negative and positive oscillations of rapidly decreasing amplitude. It is expected that the accelerometer will detect only the first few oscillations of any wave train associated with a particular collisional event. Negative accelerations are interpreted as part of a wave train belonging to a previous positive acceleration and are hence discarded in terms of registering distinct vents. Subsequent positive oscillations in a wave train are expected to be highly damped due to the low elasticity and high damping properties of the liner and the outer shell. Hence it is reasonable that each sequence of positive acceleration defines a vibrational event caused by a particular media/media or media/liner collision within the mill.

The various measures used to characterise surface vibrational waves are as follows:

1. Mean and standard deviation of the sampled signal.
2. Power spectral density of the sampled signal.
3. Histograms of sampled signal amplitude. This includes histograms of sampled signal, absolute value of sampled signal and the natural logarithm of the absolute value of the sampled signal.
4. Total number of signal samples and the ratio of large to small amplitude samples. The cut-off amplitude between large- and small-scale accelerometer responses is user defined.
5. Mean and standard deviation of the amplitude of surface vibrational events.
6. Mean and standard deviation of the phase (in terms of the position of the accelerometer in the rotation cycle of the mill) of surface vibrational events.
7. Mean and standard deviation of the phase (in terms of the position of the accelerometer in the rotation cycle of the mill) weighted by amplitude of surface vibrational events.
8. Histograms of surface vibrational event magnitude. This includes histograms of amplitude and the natural logarithm of the amplitude of events
9. Total number of events and the ratio of large to small amplitude events. The cut-off amplitude between large- and small-scale accelerometer responses is again user defined.
10. The energy of the sampled signal as derived from the power spectral density, in the frequency bands 0–100 Hz, 100–300 Hz and 500–700 Hz and around 18 kHz. These frequency bands are deemed by experience to contain most of the surface vibrational wave energy information that varies with mill operating conditions.
11. The total energy of the sampled signal derived from both the power spectral density and the amplitude versus time accelerometer response.
12. Contour plot of vibrational event numbers as a function of SAG mill phase angle and event amplitude. Event amplitude and phase angle are identified as associated with the maximum positive excursion of the accelerometer response for any particular event. The natural logarithm of surface vibrational event numbers is plotted in order to emphasise the position angle of relatively large amplitude but infrequent events.
13. Spectrogram time-dependent frequency analysis of the sampled signal.
14. Decimated (decreased sampling rate) versions of the signal and associated power spectral density analysis.

All the above measures are derived for each revolution of a continuous monitoring period and over the entire integral number of mill revolutions of the same. The signal analysis software has been implemented in the MATLAB technical computing language. However, any and all of the components of the software could be implemented in —a variety of other programming languages.

Figure 3A:
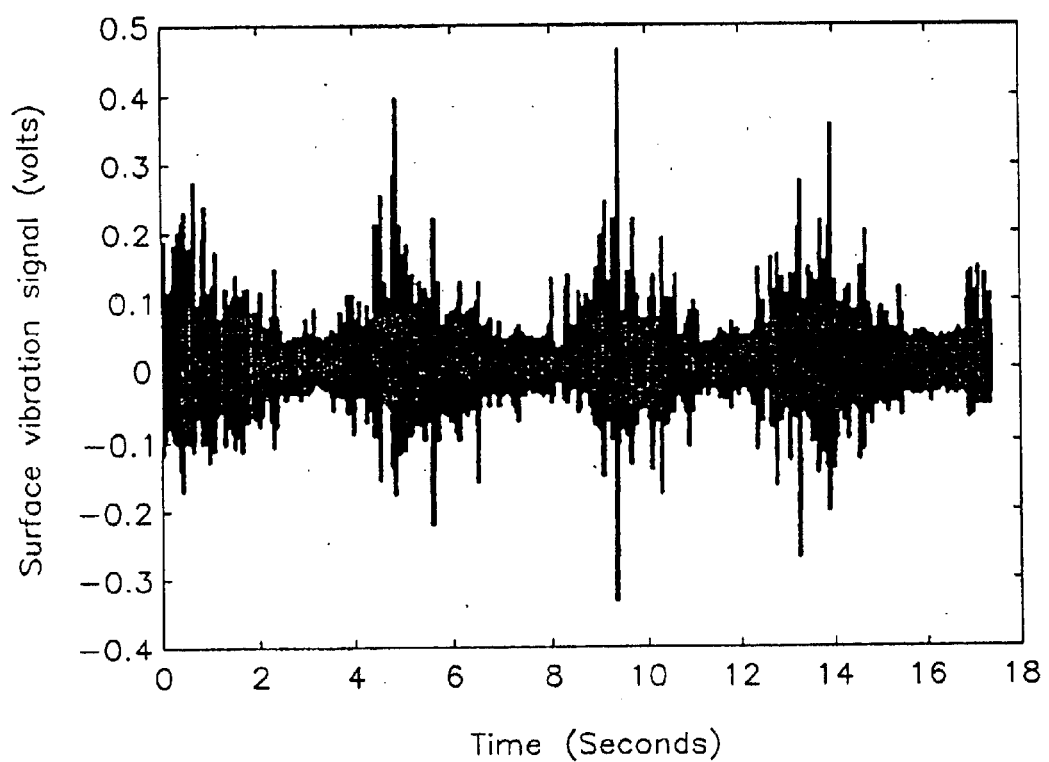
FIG. 3a shows a graphical representation of an accelerometer response on a rotating SAG Mill as a function of time.

A typical accelerometer response trace as a function of lime for a rotating SAG mill is shown below (FIG. 3). In this case four full mill revolutions of data ($5 \times 10^4$ samples per second), previously defined as a long run, are recorded. There is clear evidence of periodicity in the amplitude of events registered by a single accelerometer as a function of mill rotation angle.

Figure 3B:
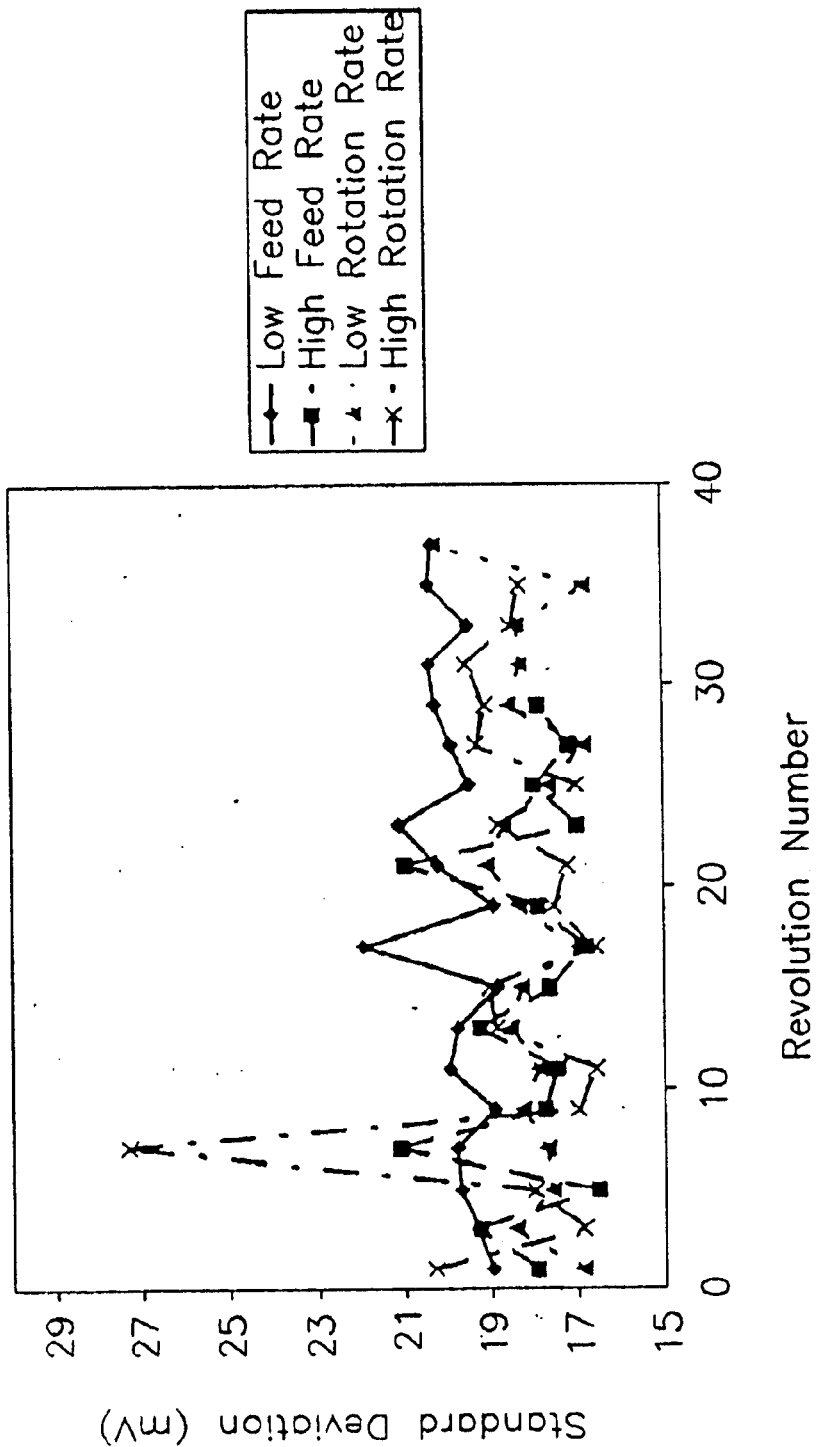
FIG. 3b shows a plot of standard deviation of sampled signal as a function of mill revolution number. Manipulated variables are feed rate and mill rotation speed.
Figure 3C:
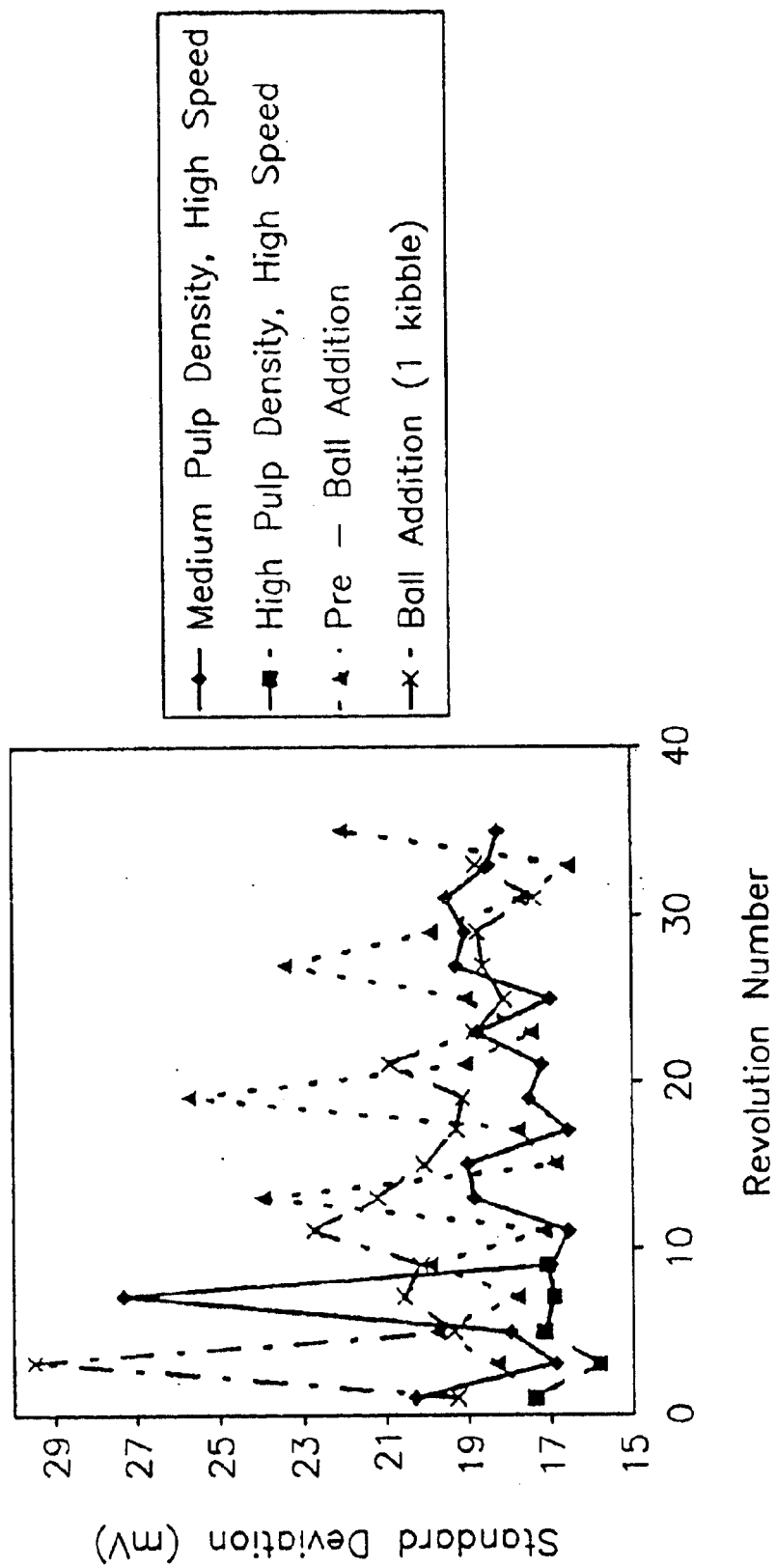
FIG. 3c shows standard deviation of the sample signal as a function of mill revolution number. Manipulated variables are pulp density and ball addition.

The standard deviation of the surface vibration sampled signal is an important measure of the condition of the material within the moving machine. FIGS. 3b and 3c show the standard deviation of the sampled signal from a SAG mill over a single revolution as a function of mill revolution number for a range of manipulated operating variables. FIG. 3b shows that on average, the signal standard deviation is substantially higher at the low rather than the high feed rate and at the high rather than the low mill speed. The former result is thought to indicate a low filling level under low feed rate conditions at dynamic steady state and hence relatively poor cushioning of high energy grinding media impact events on the liner. The latter is thought to be due to the increase in both energy and frequency of grinding media impacting directly on the liner.

FIG. 3c shows that the addition of balls actually decreases the variability of the standard deviation across mill rotation periods, but increases its mean value. FIG. 3c also shows that at high speed, a high pulp density condition leads to a decreased standard deviation. This may be due to increased dampening of grinding media collisions with pulp density. At low speeds the standard deviation actually increases with pulp density. Both FIGS. 3b and 3c demonstrate considerable quasi-periodic variability of the signal standard deviation between rotation periods. This may be due to non-steady motion of the total charge at frequencies less than or equal to the rotation of the mill, even when dynamic steady state power draft conditions apply.

A polar contour plot of vibrational event numbers as a function of SAG mill rotation phase angle and event magnitude allows vibration events to be identified with particular locations in the rotation cycle. Differences may be identified in SAG mill operation both between rotation periods and with changes in mill operating conditions. The position of either the event amplitude or energy weighted average phase angle of acoustic events is a simple and valuable quantitative measure in this regard.

Figure 4A:
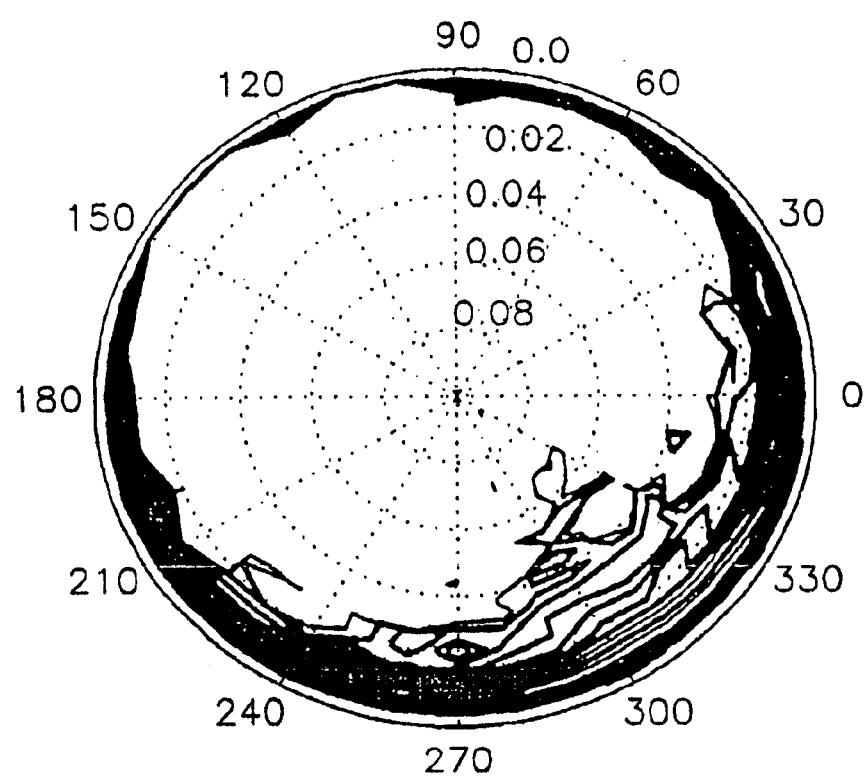
FIG. 4a shows a low rotation rate polar contour plot of the natural logarithm of a number of vibrational events ($E^{0.5}$ number intervals) as a function of energy (volts$^2$) in the radial direction and mill rotation phase angle (degrees anti-clockwise from the 3 o'clock position) in the azimuthal direction. Contours of large numbers of events are at low amplitudes. The mill is rotating clockwise.

FIG. 4a shows a surface vibration (loosely termed acoustic emission or AE) event numbers polar contour plot for an "average" SAG mill revolution, based on 19 single revolutions of data obtained under low speed experimental conditions. There is clear evidence of the expected localisation of large events in regions where the charge is thought to be in contact with the liner. In particular, there are greater numbers of relatively high-energy events in the ~290–330 degrees region where it is expected that cataracting media impact on the charge. These events are thought to identify the position of the "toe" of the charge. Hence it is inferred that there is strong damping of AE waves as they propagate around the shell. However, FIG. 4a also shows that there is a registration of lower strength AE events in regions where the charge and grinding media are not expected to be in contact with the shell liner. These lower energy signals are most likely due to surface AE waves propagating around the shell from other regions. The prominence of these signals at positions above that expected for the "toe" of the charge is in accordance with the view that as the sensor rotates through these positions it is actually registering events that have originated further down the shell. Nevertheless, it seems likely that very high-energy events recorded by the accelerometer at a particular phase angle do reflect collisions in the adjacent region of the inner liner. The identification of the boundaries of contact of the SAG mill charge with the liner is potentially important as this information may be used to deduce the charge volume and hence indicate changes in internal conditions as changes in operating conditions occur.

Figure 4B:
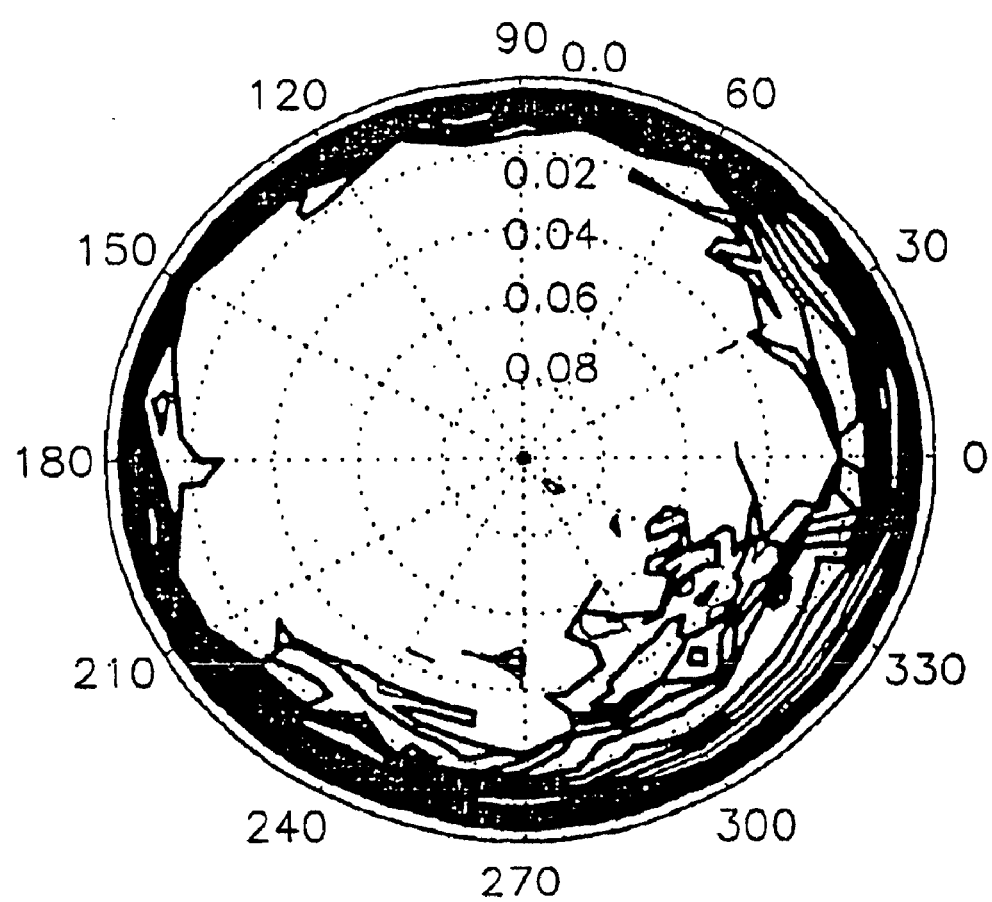
FIG. 4b shows a high rotation rate polar plot of the natural logarithm of the number of vibrational events ($E^{0.5}$ number intervals) as a function of energy (volts$^2$) in the radial direction and mill rotation phase angle (degrees anti-clockwise from the 3 o'clock position) in the azimuthal direction. Contours of large numbers of events are at low amplitudes. The mill is rotating clockwise.

FIG. 4b is an AE event numbers polar contour plot for high rotation rate conditions (14.5 rpm, 72% pulp density and 210 t/h). The high-energy events have now clearly split into two peaks at ~290 degrees and ~330 degrees (this is even clearer for plots based on individual rotation periods). These peaks are postulated to represent respectively the "toe" of the charge and a region where cataracting grinding media directly impinge on the liner. The monitoring technique can therefore discriminate large energy impacts above the "toe" of the charge. This detection of grinding media direct impacts on the liner can be used as a predictor of liner wear rate.

FIG. 4c shows the amplitude weighted average AE event phase angle over a revolution as a function of revolution number. As expected from examining FIGS. 4a and 4b, the average event phase angle is in the quadrant associated with the "toe" of the charge. There are clear differences between the average phase angle for the different operating conditions previously mentioned. The average position angle associated with low feed rate conditions is substantially less than the same measure for high feed rates. This is physically reasonable, as one would expect the steady state volumetric loading to be less under low feed rate conditions. The average phase angle for a high rotation rate is clearly larger than the corresponding measure for a low rotation rate. Again, this is physically reasonable as one would expect a high rotation rate to result in more grinding media impacting higher up the liner wall. Increasing the pulp density or adding grinding balls while maintaining other operating conditions lowers the average position angle. These are plausible results if increases in pulp density and ball addition are considered to stabilise the bulk behaviour of the charge. The significant changes in average event phase angle that occur with mill rotation number may indicate bulk movement of the charge.

Figure 5:
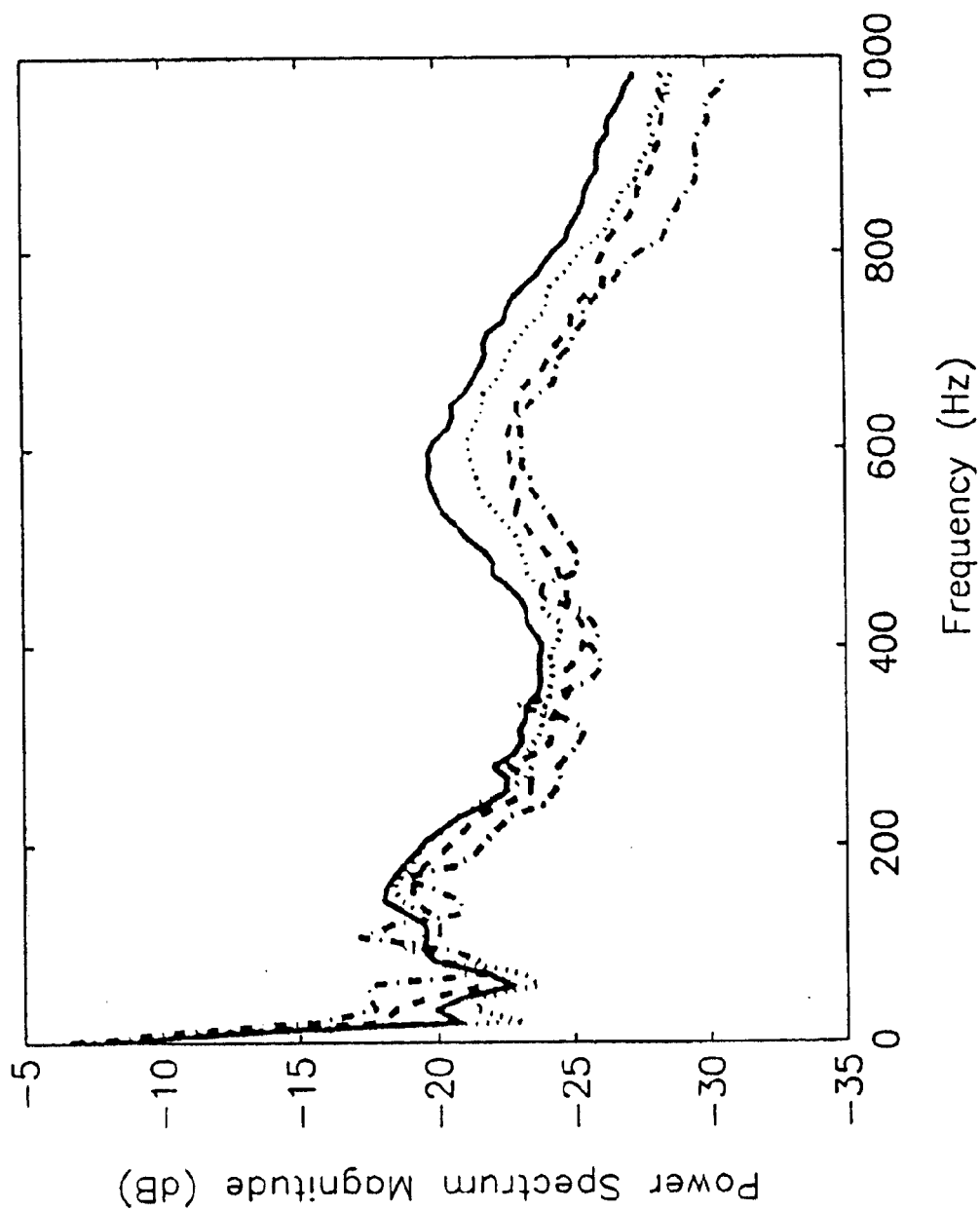
FIG. 5 shows a graphical representation of power spectral density plot upto 1,000 Hz, the parameters are $2^{16}$ FFT length, $2^{15}$ number of samples overlap, FFT length Hanning windowing and nil detrending.

FIG. 5 shows a typical power spectral density plot obtained for surface vibration waves detected by an accelerometer, based on the same set of data. Spectral features are readily apparent near the DC channel (<100 Hz), around 100–200 Hz and near 600 Hz. Finer spikes in the power spectrum can be seen at frequencies below about 400 Hz. FIG. 4d shows PSD plots for extremes in mill speed and feed rate. Spectral features that are sensitive to mill operating conditions are apparent for frequencies <100 Hz, around 100–200 Hz and near 600 Hz. Surface vibration power is higher at low feed rates at frequencies >~100 Hz. High mill speeds result in increased surface vibration power at low frequencies (<~100 Hz). The total power associated with the signal PSD is substantially higher for both the low feed rate (~40%) and high speed (~30%) operating conditions in comparison with values for the respective high feed rate and low speed operating conditions. Sharper spikes in the power spectrum can be seen at frequencies below ~500 Hz in the case of high mill rotation speed. All these features are well above the background noise level and are probably related to bulk motion of the charge. In FIG. 5, the frequency range was restricted to a maximum of 1000 Hz, because ~80% of the AE signal power was within this range. Power spectral density plots have also been obtained up to the Nyqvist frequency (half the sampling rate).

Figure 6:
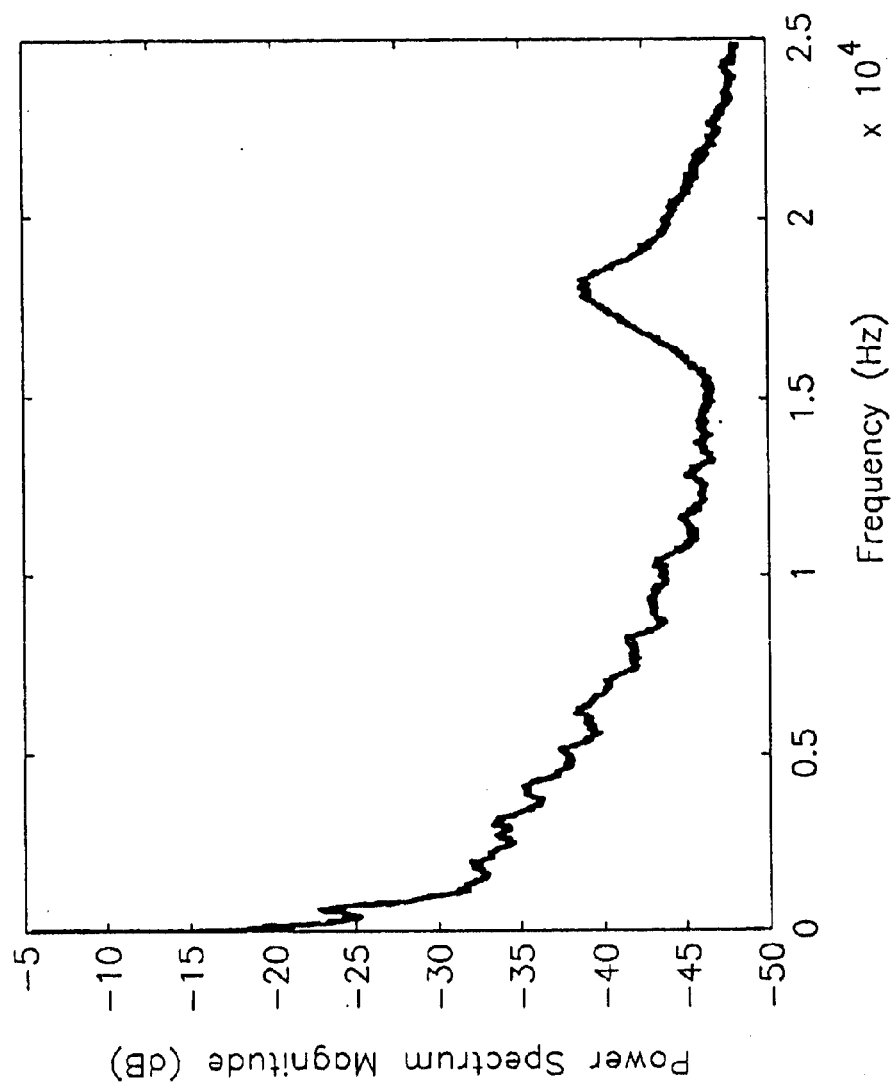
FIG. 6 shows a graphical representation of power spectral density plot upto Nyquist frequency, the parameters are $2^{10}$ FFT length, $2^9$ number of samples overlap, FFT length Hanning windowing and nil detrending.

FIG. 6 shows an example based on the same data. A prominent spectral feature is apparent at a relatively high frequency (around 18000 Hz) and experience has shown that this feature is sensitive to mill operating conditions. Fourier analysis is used in order to try to represent the accelerometer response to surface vibrational waves in terms of a superposition of sinusoidal waves at characteristic frequencies. As vibrational events are discrete entities, another fruitful approach might be wavelet analysis.

Figure 7A:
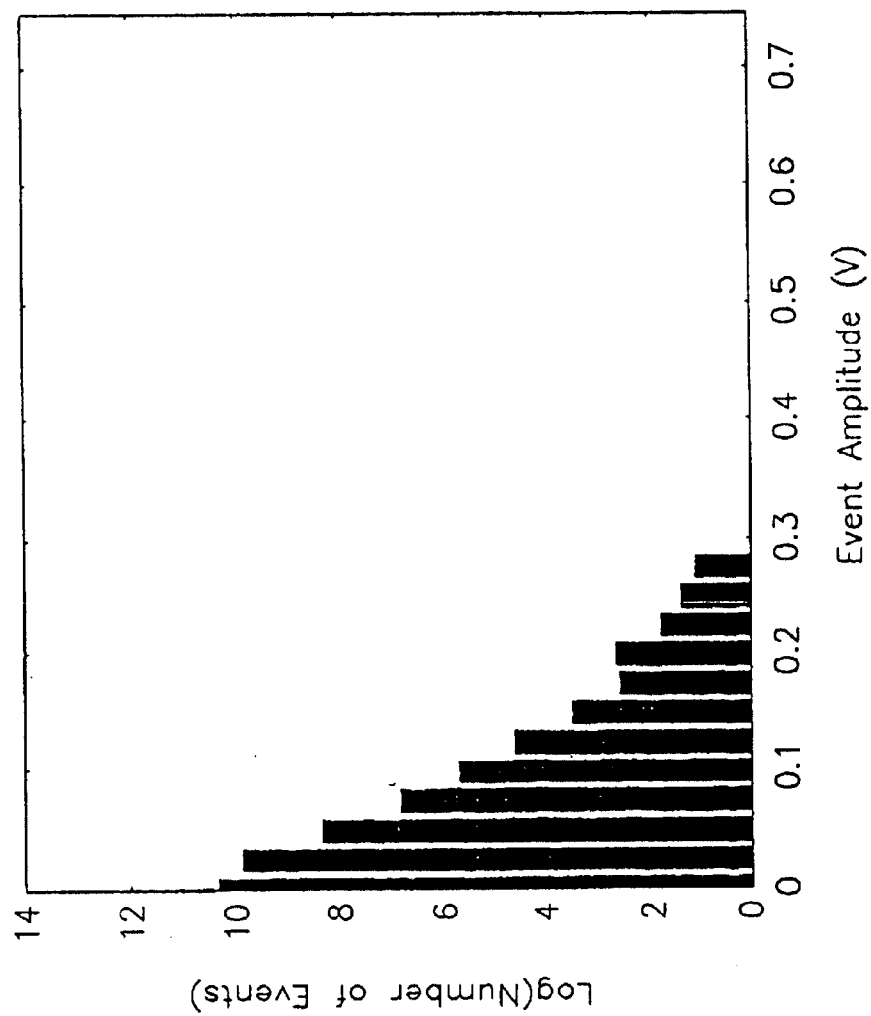
FIG. 7a shows a histogram of the natural logarithm of the total number of vibrational events occurring within an SAG Mill, as a function of event amplitude.

FIG. 7a shows a histogram of the number of vibrational events as a function of the amplitude of the accelerometer response associated with the event. This is an important way of demonstrating both the total number and distribution with amplitude of vibrational events as a function of mill operating conditions. In this manner operating conditions that lead to a relatively large number of very high amplitude vibrational events can be easily identified. Such cases correspond to conditions of high liner wear. Conversely, concentration of events at a relatively low amplitude indicate ineffective particle grinding within the SAG mill.

Figure 7B:
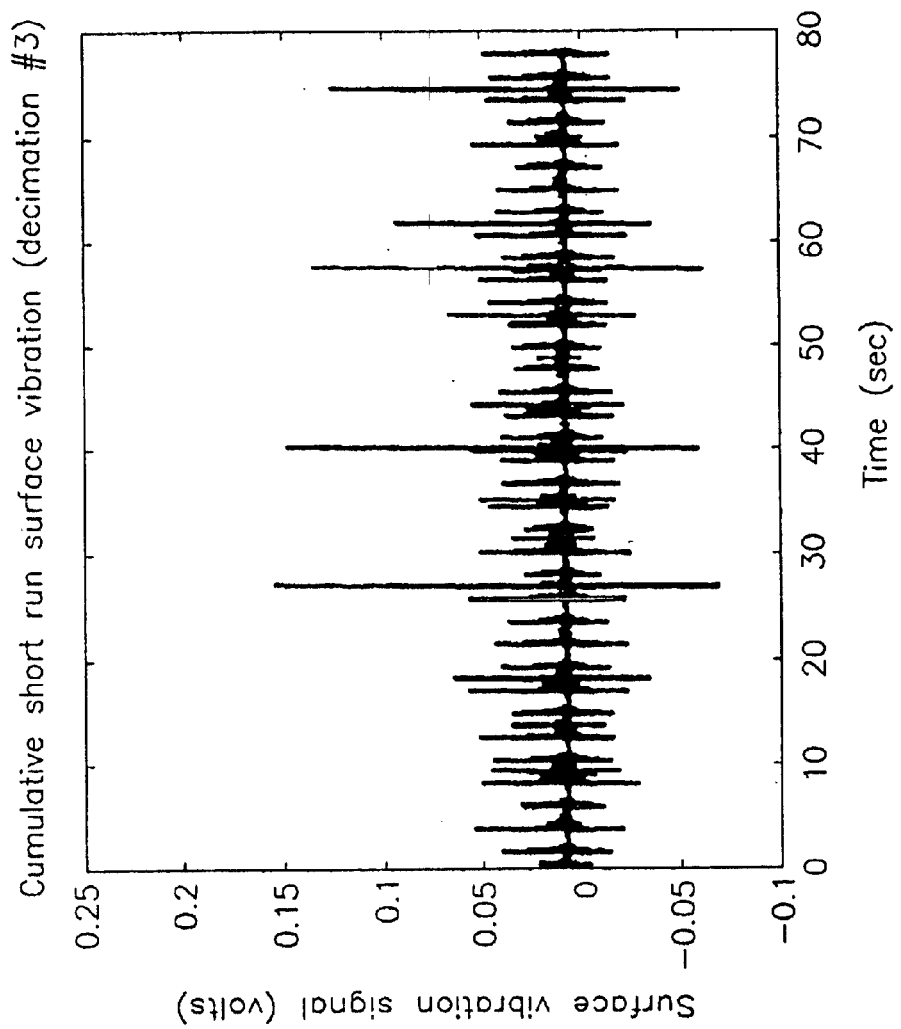
FIG. 7b shows a decimated signal for 18 revolutions of data. D cimation of raw signal by a factor of $10^3$ by successive application of factor of 10 re-sampling and filtering.
Figure 7C:
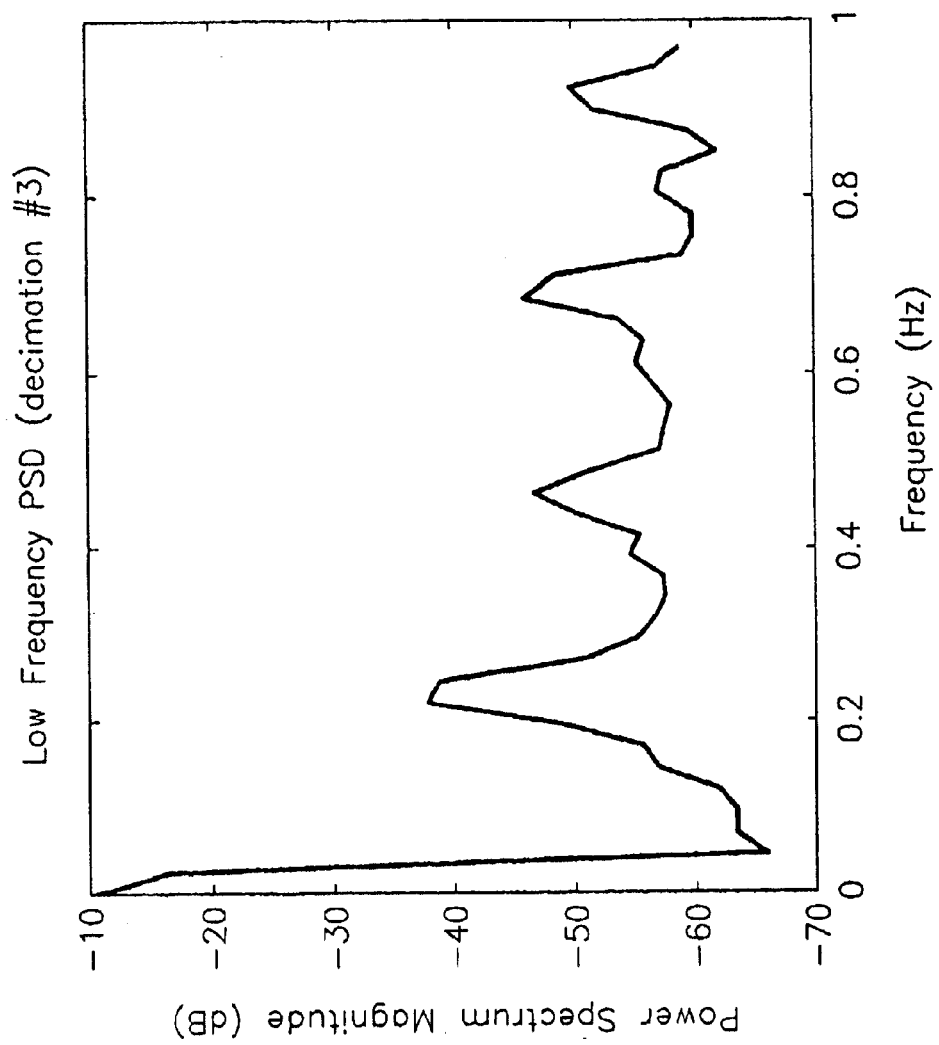
FIG. 7c shows a PSD plot upto 1 Hz from decimated signal ($2^{11}$ FFT length and Harming windowing, $2^{10}$ number of samples overlap, and nil detrending.)

Power spectral density analysis associated with multiple revolutions of surface vibration data can be used to obtain information on periodicities in charge behaviour at very low frequencies—even down to and below the frequency of rotation of the mill. The process used for this type of analysis is successive decimation of the raw sampled signal in order to decrease the sampling rate of the data. The decimation process filters the input data with a lowpass filter and then resamples the resulting smoothed signal at a lower rate. FIGS. 7b and 7c show the decimated signal and power spectral density plot obtained via decimation of eighteen revolutions of the surface vibration signal prior to the addition of grinding media. Successive decimation of the signal by factors of ten was used to reveal energy peaks at the rotation frequency of the mill (0.23 Hz) and several higher harmonics. Spectral features sensitive to mill operating conditions are present over the entire range of frequencies up to those shown in FIGS. 5 and 6.

Figure 7E:
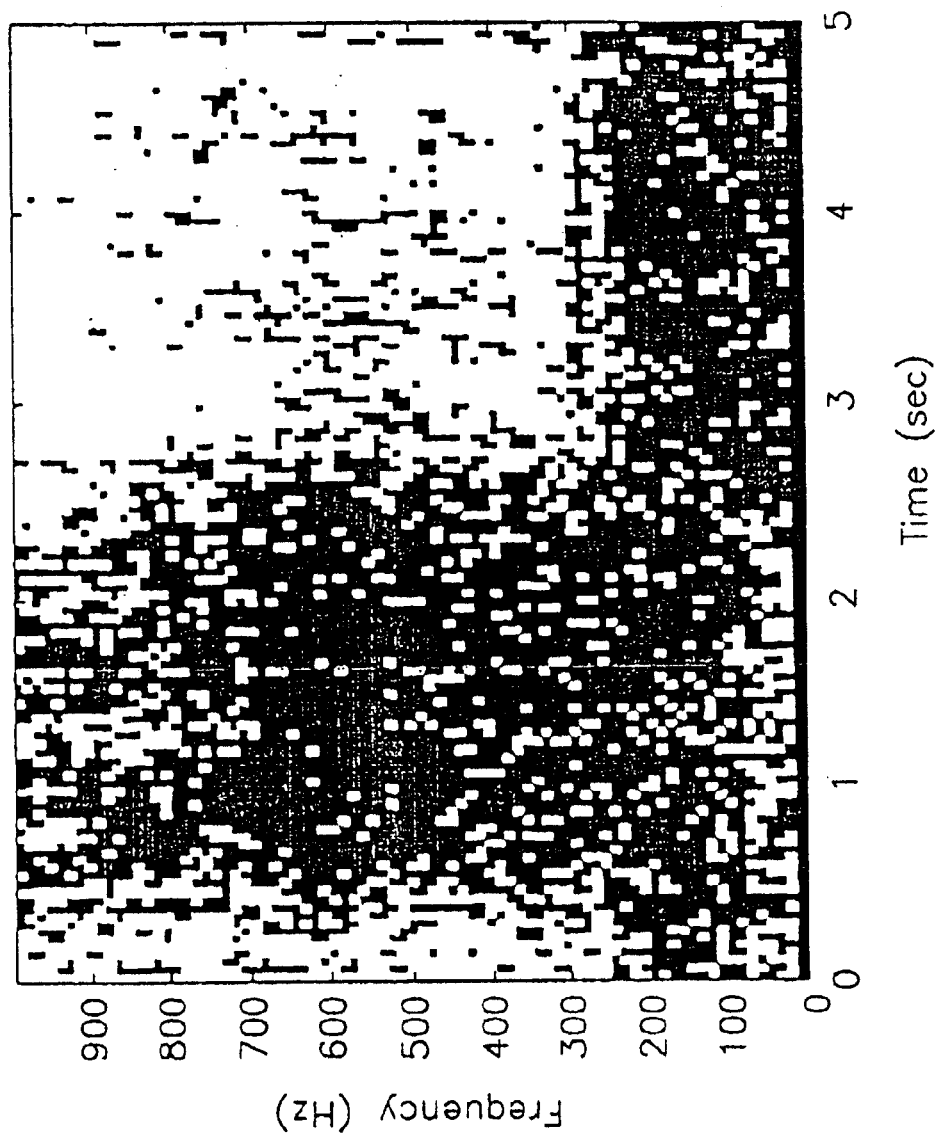
FIG. 7e shows a spectrogram plot upto 1000 Hz ($2^{12}$ FFT length and Hanning windowing, $2^{11}$ number of samples overlap, and nil detrending)

Time-dependent frequency analysis can be used to gain further knowledge of the internal behaviour of the mill. A spectrogram computes the windowed discrete-time Fourier transform of a signal using sliding windowing. FIGS. 7d and 7e are spectrograms of a single rotation period (~5 seconds) of data associated with the low feed rate mill operating condition. The colour intensity plot displays the power of the signal at each sampling frequency and time.

FIG. 7d shows strong spectral features below ~5 kHz and a distinct feature at ~1kHz. This is in accordance with power spectral density analysis as demonstrated in FIG. 6. However, such plots also show that the frequency distribution of the power of the signal is not the same at all times over a rotation period. This is more clearly demonstrated in FIG. 7e, which shows that power in the range ~200–1000 Hz is largely restricted to a distinct time range in the mill rotation period. The spectral feature at ~600 Hz previously identified by power spectral density analysis can therefore be used as a measure of the boundaries of the charge during the mill rotation period, corresponding to both the 'shoulder' and 'toe' position of the charge. Analysis of spectrogram (and power spectral density) plots over many rotation periods and for different mill operating conditions reveals the sensitivity of these measures to operating conditions. Spectrogram plots can also be represented in a polar fashion (similar to FIGS. 4a and 4b) in order to directly determine the shoulder and toe positions in terms of phase angles.

The boundaries of the SAG mill charge as determination of the weighted average surface vibration event phase angle can then be used to provide a first approximation for the volumetric filling of the mill. Simple geometrical considerations lead to the following $$f = \frac{(\theta - \sin\theta)}{2\pi}$$

expression for the fractional filling f of the mill.

Here $\theta$ is the angle (radians) between the toe and shoulder positions of the charge.

Correlations Between Surface Vibration Measures and Mill Operating Conditions As mentioned in the previous section, mean and standard deviation of sampled signal was calculated for all test runs. It was postulated that the standard deviation would be a useful measure of activity in the mill at a given set of conditions. The traces show that the amplitude of the signals and the number of high amplitude (energy) signals changes for different conditions. These changes are then likely to change the standard deviation thereby creating an opportunity to establish relationships between the surface vibration features encompassed in the standard deviation and actual mill operating variables.

Figure 8:
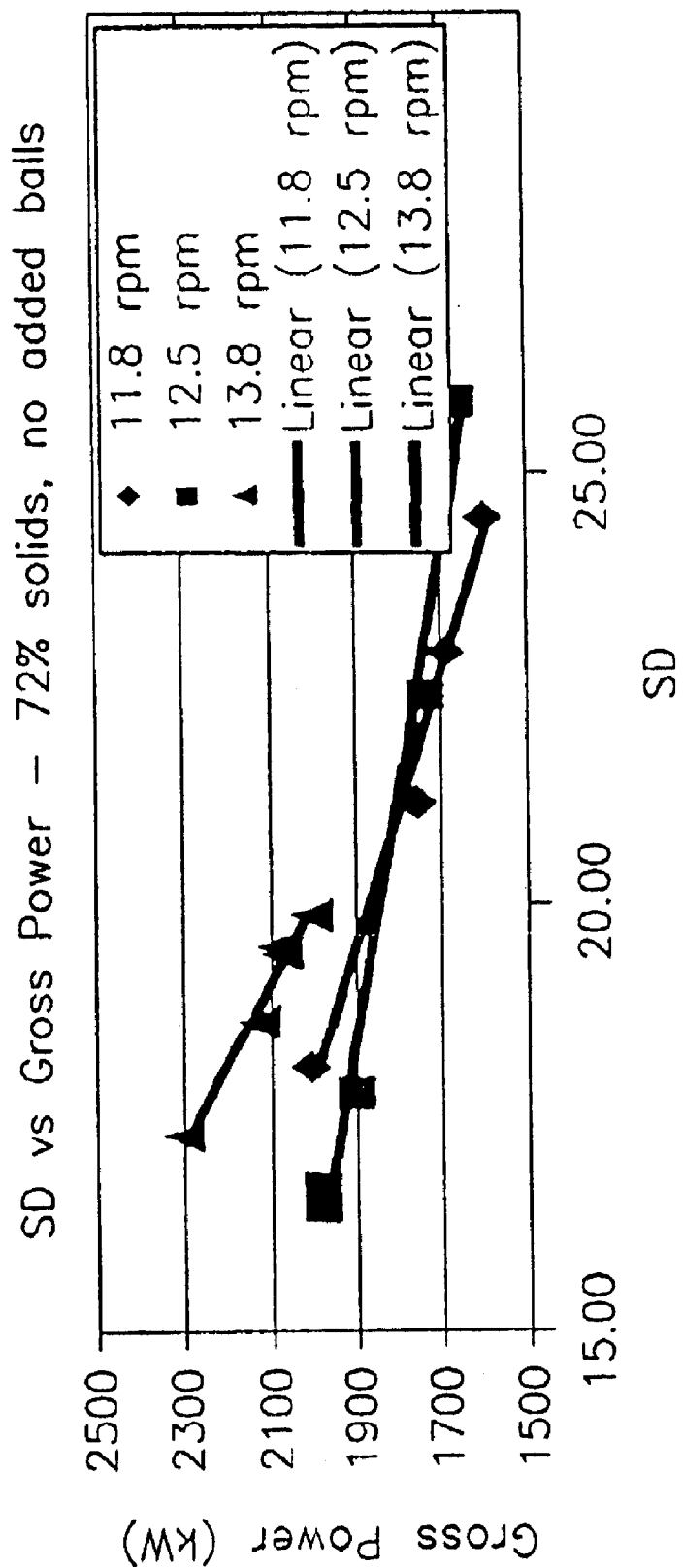
FIG. 8 shows a graphical representation of a SAG Mill gross power as a function of the standard deviation of surfaces for three different mill speed settings.

FIG. 8 shows a plot of standard deviation and mill gross power for three different mill speed settings.

Under normal operating conditions the mill gross power corresponds to the overall load level in the mill i.e the higher the gross power, the higher the load level. Other manipulated variables, namely ball addition and pulp density, were held constant. At each speed, the relationship between standard deviation and gross power is linear with a negative slope. An increase in the mill gross power (load level) leads to a decrease in the standard deviation of the signal. This result is consistent with experience where the mechanism at play is thought to be increased damping as a result of the higher load level in the mill. The fitted equation for each speed differs and is likely to be indicative of some other effects that are at work. Similar relationships are being developed for other surface vibration measures listed in the previous section. The relationships shown in FIG. 8 mean that for a given speed, the standard deviation measured relates directly to the gross power of the mill which itself is an indirect measure of the load level.

FIG. 9 shows a plot of the standard deviation against pulp density at two different mill conditions.

As expected, the relationships for the two conditions differ but are consistent with experience. Usually, at higher densities, the thicker slurry inside the mill acts as a more effective damper thereby reducing the severity of impacts on the shell. This assertion is reflected in the measured readings, which show lower standard deviation at higher density. Similarly at lower densities, higher surface vibration standard deviation was measured.

Alternative Signal Analysis and Correlation Determination Techniques

The list of signal analysis techniques used above to characterise the surface vibration signals (including techniques based on Fourier analysis, histogram, signal moment and surface vibration event analysis) is by no means exhaustive. Wavelet analysis could also be productive given that the surface vibration signals are believed to be largely due to discrete (time bounded) collision events within the mill. The cestrum analysis and homomorphic deconvolution techniques of non-linear signal processing could also be utilised to further analyse the signals. Analysis of signals from multiple sensing devices at different locations on a single moving machine could entail the use of cross correlation/cross spectral density analysis in order to identify the position of origin (and initial intensity) of a vibration.

Correlations between features of the signal and the mill operating conditions can allow the use of surface vibration signals as 'soft-sensors' for machine/process performance and estimation of unknown plant variables. Correlations determined by regression-based analysis of surface vibration signals could be extended to include consideration of relationships between operating conditions and spectral features determined by various types of Fourier and/or wavelet analysis, additional moments and statistical measures of the sampled signal and features determined by event and histogram statistical analysis. Multiple regression and principal component analysis could be used to further investigate these linkages. Other intelligent analysis methods such as neural networks, genetic algorithms, self-organising method, fuzzy logic, cluster analysis, Kalman Filter, expert system and ARMAX/NARMAX regression-based models could be used to analyse the data and seek correlations relating to both operating conditions, other process features such as the charge particle size distribution and ultimately be used for process optimisation and control.

Linkages could also be sought to discrete element models and/or other models including phenomenal logical knowledge.

Alternative Technologies and Applications

Applications of the surface vibration technique extend well beyond SAG mills to other grinding mills e.g ball mills, stirred ball mills, jet mills etc. The technique is also applicable to other comminution equipment such as crushers, impactors, and hammer mills. In fact any machine that processes material and a requirement exists for a better understanding of the mechanisms occurring inside both from a processing and condition monitoring viewpoint are potential applications of this technique. Machines, the operation of which would benefit with the application of [his technique, include but are not limited to:

a AG/SAG/ball/rod/vibratory mills
Gyratory/cone/jaw/rolls crushers
Vertical shaft impactors
Hammer mills
Vertical spindle mills
Hydrocyclones/dense media cyclones
Spirals
Vibrating/DSM/banana screens
Vibrating plate separation devices
Flotation cells
High pressure grinding rolls/ roller presses
Any equipment requiring process or condition monitoring
Rotary kilns and dryers and balling drums Alternative technologies that may, compete with this surface vibration technique are thought to be acoustic emission sensors, Le microphones, mounted on the mill and configured similarly to this technique. This set-up would allow acoustic emission features to be correlated against events occurring in the mill during each revolution. The hardware required to build this type of system, aside from the sensors, is likely to be very similar to the surface vibration system described above. Another possibility is to enclose a mill with a mounting frame so that the microphones are positioned around the entire circumference of the mill but are mounted off the mill. It is somewhat doubtful whether this configuration is practicable.

The arrangements of experimental apparatus and signal analysis techniques as applied to monitoring a SAG mill as described in this document have been advanced merely by way of explanation. Many modifications may be made thereto both for further monitoring of SAG mills and other material processing machines without departing from the spirit and scope of the invention which includes every novel feature and combination of novel features herein disclosed.

What is claimed is:

1. A system for monitoring mechanical waves from a moving machine which in operation has moving particulate matter therein, the system comprising
at least one sensor located on an exterior surface of the moving machine at a location away from the central axis of the machine, the at least one sensor sensing acoustic waves and including a transmitter for transmitting electrical signals representing the sensed waves over a predetermined period of time to a receiver at a location remote from the at least one sensor, a data processor connected to the receiver receiving signals from the receiver which signals represent the sensed waves and receiving data relating to the position of at least one sensor as the at least one sensor moves with the exterior surface of the machine and processing the signals to produce output signals for display on a display means, wherein the output signals for display represent one or more parameters indicative of mechanical waves emitted from the moving machine over a predetermined period of time.

2. The system as claimed in claim 1 wherein the receiver is located on a stationery surface separate from the moving machine.

3. The system as claimed in claim 1, further comprising a power supply for the at least one sensor is located on the moving machine.

4. The system as claimed in claim 1 wherein the data processor is adapted to produce output signals which represent a plurality of acoustic events occurring within the machine, amplitudes of the acoustic events and data relating to the position of the acoustic events.

5. The system as claimed in claim 1 further comprising at least one proximity detector for monitoring the location of the at least one sensor at a predetermined time, whereby data from the proximity switch is adapted to be communicated to the data processor.

6. The system as claimed in claim 1 wherein the data processor includes a timing means for calculating the location of the at least one sensor at a predetermined time.

7. The system as claimed in claim 1 wherein the at least one sensor includes an accelerometer which is adapted to transmit data relating to the frequency of vibrational events occurring within the machine and the amplitude of the vibrational events at particular locations within the machine to the transmitter.

8. A method of analysing operational parameters of a machine having a moving particulate material therein, the method comprising the steps of
recording data representing a number of mechanical events occurring within the machine over a predetermined period of time, the amplitude of the mechanical events occurring over the predetermined period of time and positional data relating to the position of the mechanical events occurring within the machine,
displaying a graphical representation of the recorded data, the graphical representation including parameters relating to the number of mechanical events, the amplitude of mechanical events and the position of mechanical events occurring within the machine during the machines operation, and
the graphical representation of recorded data including mean and standard deviation of vibrational events occurring within the machine, power spectral density of vibrational events occurring within the machine and histograms of amplitude of vibrational events occurring within the machine.

9. The method as claimed in claim 8, further comprising the step of measuring volumetric load of the particulate matter within the machine by identifying the toe and shoulder portions of the particulate matter.

10. The method as claimed in claim 9 wherein volumetric load is determined from a polar co-ordinate plot of events occurring within the machine.

11. The method as claimed in claim 10 wherein volumetric load is calculated for a range of angles in which events within the machine have greatest deleterious effect on the interior of the machine.

12. The method as claimed in claim 11 wherein a value for volumetric filling of the mill is produced from the recorded data and the value of volumetric filling $$f = \frac{(\theta - \sin\theta)}{2\pi}$$

where θ is the angle (radiance) between the toe and shoulder positions of the particulate matter.

13. A method of controlling operational parameters of a machine having a moveable substance therein, the method comprising the steps of
recording data representing a number of vibrational events occurring within a machine over a predetermined period of time, amplitude of the vibrational events occurring over the predetermined period of time and position data relating to the position of the vibrational events over the predetermined period of time, and
determining zones within the machine which are subject to predetermined levels of wear and altering the machine operational characteristics to reduce the levels of wear for the zones.

14. A method of identifying the volumetric load of particulate matter within a machine comprising the steps of
receiving data, representing a number of mechanical events occurring within the machine over a predetermined period of time, the amplitude of the mechanical events occurring over the predetermined period of time and positional data relating to the position of the mechanical events occurring within the machine, and
processing the received data to identify toe and shoulder positions of the particulate matter within the machine whereby the location of maximum deterioration of an inside surface of the machine can be minimized.

15. The method as claimed in claim 14 wherein data is received for a plurality of speeds of the machine.

16. The method as claimed in claim 15 including the step of identifying the fractional filling f of the machine where $$f = \frac{(\theta - \sin\theta)}{2\pi}$$

with $\theta$ being the angle (radiance) between the toe and shoulder positions of the charge.

17. A system for monitoring mechanical waves from a moving machine which in operation has moving particulate matter therein, the system comprising
at least one sensor located on an exterior surface of the moving machine at a location away from the central axis of the machine, the at least one sensor sensing acoustic waves and including a transmitter for transmitting electrical signals representing the sensed waves over a predetermined period of time to a receiver at a location remote from the at least one sensor, a data processor connected to the receiver for receiving signals from the receiver which signals represent the sensed waves and processing the signals to produce output signals for display on a display means, wherein the output signals for display represent one or more parameters indicative of mechanical waves emitted from the moving machine over a predetermined period of time, and a plurality of the at least one sensor being spaced around a periphery of the moving machine to enable polar co-ordinates of an origin of emissions to be located.

18. The system as claimed in claim 17, wherein the plurality of sensors are equispaced around the periphery of the moving machine.

19. The system as claimed in claim 17, wherein the plurality of sensors are arranged in an array around the moving machine and along a length of the moving machine to enable a three dimensional co-ordinate axis to be plotted of a location of an origin of omissions from the moving machine.

* * * * *